US011266145B2

(12) United States Patent
Johnson

(10) Patent No.: US 11,266,145 B2
(45) Date of Patent: *Mar. 8, 2022

(54) COMPOSITIONS COMPRISING PROTOCATECHUIC ACID AND METHODS OF USE

(71) Applicant: Lanny L Johnson, Frankfort, MI (US)

(72) Inventor: Lanny L Johnson, Frankfort, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/947,256

(22) Filed: Jul. 24, 2020

(65) Prior Publication Data

US 2022/0022452 A1 Jan. 27, 2022

(51) Int. Cl.
| | | |
|---|---|---|
| *A01N 37/40* | (2006.01) |
| *A61P 31/14* | (2006.01) |
| *A61K 31/192* | (2006.01) |
| *A61K 9/00* | (2006.01) |
| *A01N 25/02* | (2006.01) |
| *A61L 2/22* | (2006.01) |
| *A61L 2/00* | (2006.01) |
| *A61L 101/36* | (2006.01) |

(52) U.S. Cl.
CPC ............ *A01N 37/40* (2013.01); *A01N 25/02* (2013.01); *A61K 9/0014* (2013.01); *A61K 31/192* (2013.01); *A61L 2/0088* (2013.01); *A61L 2/22* (2013.01); *A61P 31/14* (2018.01); *A61L 2101/36* (2020.08); *A61L 2202/23* (2013.01); *A61L 2202/24* (2013.01); *A61L 2202/25* (2013.01); *A61L 2202/26* (2013.01)

(58) Field of Classification Search
CPC ........ A01N 37/40; A61P 31/14; A61K 31/192
See application file for complete search history.

(56) References Cited

U.S. PATENT DOCUMENTS

| 2007/0154508 A1 | 7/2007 | Patton et al. |
| 2013/0095240 A1 | 4/2013 | Parekh et al. |

FOREIGN PATENT DOCUMENTS

| CN | 104412973 | * | 3/2015 | |
| WO | WO-2004092283 A2 | * | 10/2004 | ............. A61K 33/34 |

OTHER PUBLICATIONS

Geng et al. ("Investigation on potential of Jinlianhua decoction against novel coronavirus (2019-nCoV) based on molecular docking," Open Access (OA) Online-First Publishing of Research Papers on COVID-19, 2020, 1-16, 2020).*
Shi et al. ("Study on the overall regulation of Xuebijing injection in treating coronavirus disease 2019," Open Access (OA) Online-First Publishing of Research Papers on COVID-19, 2020, 1-7, 2020).*
Isolation of protocatechuic acid from the pigmented onion scales and its significance to disease resistance in onions. By: Karl Paul Link.
Human metabolism and elimination of the anthocyanin, cyanidin-3-glucoside. By: Charles Czank, Aedi'n Cassidy, Qingzhi Zhang, Douglas J Morrison, Tom Preston, Paul A Kroon, Nigel P Botting, and Colin D Kay.
The pharmacokinetics of anthocyanins and their metabolites in humans. By: British Journal of Pharmacology.
Protocatechuic acid is the major human metabolite of cyanidin-glucoside. By: Journal Nutrition.
Cyanidins: metabolism and biological properties. J Nutr Biochem By: The Journal of Nutritional of Biochemistry.
Anthocyanin metabolites in human urine and serum. By: British Journal of Nutrition.
The Tissue Distribution and Urinary Excretion Study of Gallic Acid and Protocatechuic Acid after Oral Administration of Polygonum Capitatum Extract in Rats. By: Molecules.
In vitro metabolism of anthocyanins by human gut microflora. By: ResearchGate.
Antiglycative effects of protocatechuic acid in the kidneys of diabetic mice. By: Journal of Agricultural and Food Chemistry.
Diet supplements, resveratrol and protocatechuic acid, do not disturb wellness and liver morphology in rats. By: Med. Weter.
Pharmacological activities of protocatechuic acid. By: Acta Poloniae Pharmaceutica.
Antioxidant Activity and Mechanism of Protocatechuic Acid in vitro. Functional Foods in Health and Disease. By: Research Open Access.
Antioxidant activity of 3,4-DHPEA-EA and protocatechuic acid: a comparative assessment with other olive oil biophenols. By: Redox Report.
Dose translation from animal to human studies revisited. By: FASEB Journal.
Toxic dose of a simple phenolic Ie, protocatechuic acid, attenuates the glutathione level in ICR Mouse liver and kidney. By: J. Agric Food Chem.
Protocatechuic Acid as a Topical Antimicrobial for Surgical Skin Antisepsis. By: JBJS Open Access.
Cytotoxicity of crystals involves RIPK3-MLKL-mediated necroptosis. By: Nature Communications.
Involvement of oxidative stress in protocatechuic acid-mediated bacterial lethality. By: Wiley Microbiologyopen.
Spontaneous deformation of protocatechuic acid monohydrate crystals: crystallographic aspects. By: Proc. R. Soc. Lond.

(Continued)

*Primary Examiner* — Yong S. Chong
(74) *Attorney, Agent, or Firm* — Stonebridge IP, PLLC

(57) ABSTRACT

This disclosure is directed to methods of using compositions comprising protocatechuic acid (PCA) to kill virus including a Covid-19 virus. The compositions generally comprise protocatechuic acid, a liquid vehicle, and a stabilizer. In embodiments, the liquid vehicle comprises an alcohol and/or water. In preferred embodiments, the oil is an essential oil. In embodiments, the compositions may comprise principally protocatechuic acid, liquid vehicle, and stabilizer as the main ingredients. The compositions may be sprayed onto various products and articles of manufacture, and mammalian and human skin, to kill virus including a Covid-19 virus and to further protect the product or human skin for a period of time up to 24 hours or more. In preferred embodiments, an alcohol component kills virus on contact, and after drying, the residual surface PCA coating provides a continuing anti-viral function.

25 Claims, No Drawings

(56) References Cited

OTHER PUBLICATIONS

Antiviral Activities of *Hibiscus sabdariffa* L. Tea Extract Against Human Influenza A Virus Rely Largely on Acidic pH but Partially on a Low-pH-Independent Mechanism. By: Food and Environmental Virology.
Battle Against Coronavirus: Repurposing Old Friends (Food Borne Polyphenols) for New Enemy (COVID-19). By: ChemRxiv.
Data on docking of phytoconstituents of Actinidia deliciosa on dengue viral targets. By: Data in Brief.
Protocatechuic acid (PCA) induced a better antiviral effect by immune enhancement in SPF chickens. By: Microbial Pathogenesis.
Anticoagulatory, antiinflammatory, and antioxidative effects of protocatechuic acid in diabetic mice. By: J Agric Food Chem.
Anti-inflammatory and analgesic activity of protocatechuic acid in rats and mice. By: Inflammopharmacol.
Pro-coagulant activity of phenolic acids isolated from Blumea riparia. By: NPC Natural Product Communications.
Spontaneous deformation of protocatechuic acid crystals. By: R.W. Wood, for. Mem. R.S.
Engineering Problems in the Use of Glycol Vapors for Air Sterilization. By: Burgess H. Jennings and Edward Bigg, M.D.
Protocatechuic acid. By: Wikipedia.
Lee et al (Res. Microbial. 2006, 157, 876-884). (Year: 2006). Cited in copending application No. 16822859.
Li et al (Functional Foods in Health and Disease, 2011, 7, 232-244). (Year: 2011). Cited in copending application No. 16822859.
Mandalari G, Antimicrobial potential of polyphenols extracted from almond skins, 2010, Letters in Applied Microbiology, 51, 83-89 ( Year: 2010). Cited in copending application No. 16822859.
Santa Cruz Biotechnology MSDS (http://datasheets.scbt.com/sc-205818.pdf, Oct. 3, 2009). (Year: 2009). Cited in copending application No. 16822859.
C. B. Ou, Q. Pang, X. Chen, N. Hou, and C. He. Abstract, Protocatechuic acid, a new active substance against the challenge of avian infectious bursal disease virus. Poultry Science 2012. Jul:91(7):1604-9. doi: 10.3382/os.2011-02069.
PCT International Search Report, international appl. No. PCT/US2021/033357, dated Jun. 22, 2021.
PCT Written Opinion of the International Searching Authority, international appl. No. PCT/US2021/033357, dated Jun. 22, 2021.
PCT International Search Report, international appl. No. PCT/US2021/033345, dated Jun. 30, 2021.
PCT Written Opinion of the International Searching Authority, international appl. No. PCT/US2021/033345, dated Jun. 30, 2021.

\* cited by examiner

COMPOSITIONS COMPRISING PROTOCATECHUIC ACID AND METHODS OF USE

BACKGROUND OF THE DISCLOSURE

Field of the Invention

This disclosure is generally directed to compositions comprising protocatechuic acid and methods of using compositions comprising protocatechuic acid (PCA) to inactivate COVID-19 virus SARS CoV-2 and to interrupt its disease transmission, provide a treatment and enhance the translation to clinical application.

Description of the Related Art

The COVID-19 virus SARS CoV-2 has brought on an international pandemic. The World Health Organization named this new coronavirus SARS-CoV-2, and the disease, COVID-19 (CoronaVirus Disease-19). Corona viruses are common and have been recognized for many years. People around the world commonly get infected with human coronaviruses: 229E, NL63, OC43, and HKU1. However, it has become apparent that the SARS-CoV-2 is unlike any other coronavirus; i.e; MERS, SARS-CoV, and the common cold. SARS-COV-2 is unique clinically in that it is highly contagious. It rapidly became a pandemic and it is very aggressive. It affects not only the respiratory system but there are pathological manifestations in the skin, brain, liver and kidney as well SARS-CoV-2 differs in molecular structure from other coronavirus. It is known that prion-like domains exist with a distribution in the coronavirus that are unlike prion-like domains in other viruses and which may play important functional roles in transmission. The introduction of the prion to the molecular structure of the SARS-CoV-2 may require a different and unique therapeutic reagent or method. Prion is a term first used to describe the mysterious infectious agent responsible for several neurodegenerative diseases found in mammals, including Creutzfeldt-Jakob disease (CJD) in humans. The word itself derives from 'proteinaceous infectious particle' and it refers to the initially heretical hypothesis that the infectious agent causing those diseases consists only of protein with no nucleic acid genome. All previously known pathogens contain nucleic acids, which enable them to reproduce. The prion hypothesis explained why the mysterious infectious agent is resistant to ultraviolet radiation, which breaks down nucleic acids, but is susceptible to substances that disrupt proteins.

The clinical manifestations of SARS Co-2 are unique and differ from other respiratory virus. SARS Co-2 is very contagious. At the same time the clinical manifestation may vary from no symptoms, mild symptoms and for some very severe symptoms and or death. Although the primary pathology is in the respiratory system (a lung infection), this new virus has new and expanded clinical manifestations beyond prior coronal viral observations including pulmonary modes. In addition, there have been heart, skin, and brain manifestations with this virus. Its clinical manifestations may also include a severe inflammatory component called a "cytokine storm" in the lungs.

There is also thrombosis in other areas of the body beyond the lungs that has resulted in amputation of the limbs. The numbers of those infected and those dying is large.

COVID-19 is thus a pathological and clinical enigma. The is no known prophylactic drug. There is no specific therapeutic drug. There is no drug or treatment with the present prospect of translation to clinical practice. The present scientific therapeutic measures are limited to testing and tracking after which recommendations can be made for social distancing and face masks. Quarantines have been used. State and local governments have mandated non-essential business shut downs and limited public gatherings. These are after the fact measures and none are therapeutic. Testing or tracking of an entire population is not realistic and, in any case, false positives and negatives exist with all testing. Add to that that the pre-symptomatic patient is a likely cause of transmission before they have recognizable symptoms. In addition, it is recognized that there are certain subjects, perhaps 20% of those with the disease that are super spreaders yet are only identified after the fact. The fact remains that COVID-19 is not well understood and is highly contagious.

While waiting for an FDA approved drug and a vaccine, the humanitarian and societal costs in morbidity and mortality climb. The pandemic is rapidly evolving and there is every expectation it will continue since the epidemiology of this new strain is yet to be established. Even though its identification was established, the virus has spread globally, causing thousands of deaths and having an enormous impact on international health systems and economies. Testing is being developed and expanded. However, the asymptomatic have not been included in the testing protocol so a definitive understanding of SARS-CoV-2 epidemiology is lacking. The data is yet to be sufficient to rule out the false positives since those that had a cold in the past had the coronavirus. The false negatives are yet to be defined.

The only present means of containing this very contagious virus is by mitigation. There is no known established treatment. Prevention is currently limited to the use of sanitizers and disinfectants. Sanitizers typically use alcohol which is only bactericidal or veridical when wet. Upon drying there is no further anti-microbial effect. The dry surface is vulnerable to another microbial residence. In addition, there is a substantial lack of knowledge and misuse of disinfectants in the general population. Traditional disinfectants may use antimicrobials which function chemically or biochemically. Their biochemical inter-action disrupts the viral interaction with the host and/or physically disrupts the virus prongs or wall.

Crystals themselves provide a therapeutic application by their physical nature. They have known cytotoxic properties which can achieve a therapeutic result. It is known that the physical properties of crystals can have an antimicrobial property independent or in conjunction with their biochemical properties. Their many sharp edges have the potential to physically disrupt a microbe's integrity.

The coronaviruses are particularly physically vulnerable. The covering of the coronavirus is surrounded by many projections like a crown. The projections are called prongs or spikes. These spikes are the virulent contact agent with the host cell. They penetrate the human cell and the infection is then propagated. The spikes and underlying thin wall coating of the viral body are vulnerable to physical disruption. Physical disruption is one potential method of stopping the cellular invasion and the clinical disease. Crystals have a physical structure that is irregular, rough, and sharp with potential to physically disrupt a microbes' spikes and covering.

Accordingly, there is a need and an opportunity for prevention and treatment to expand beyond or in conjunction with the chemical methods to one that is physical disruption and one that is effective against in spite of various prion mutations. The use of crystals presents the possibility of creating an antiviral agent capable of protecting from or destroying SARS-CoV-2.

Protocatechuic acid crystals like other crystals are typically observed and considered only in the dry state. However, it known that PCA retains various crystalline shapes while in a liquid medium. The PCA crystal was first reported in liquid to be in three different forms in 1949. The following publication from 1949 is extensively illustrated. See https://royalsocietypublishing.org/doi/10.1098/rspa.1949.0064 Robert Williams Wood. Published: 22 Jun. 1949. https://doi.org/10.1098/rspa.1949.0064.

In 1983, Agmon, et al supported Wood's work and showed that some crystalline shapes were stable in form and other were rapidly changing in liquid. See Agmon I, Herbstein F H, Thomas J M. Spontaneous deformation of protocatechuic acid monohydrate crystals: crystallographic aspects. Proc. R. Soc. Lond. 1983. A387311-330. http://doi.org/10.1098/rspa.1983.0062.

SUMMARY OF THE INVENTION

This disclosure is generally directed to compositions comprising protocatechuic acid and methods of using compositions comprising protocatechuic acid (PCA) to inactivate COVID-19 virus SARS CoV-2 and to interrupt its disease transmission, provide a treatment and enhance the translation to clinical application. The compositions generally comprise protocatechuic acid in the dry state and or in liquid solution or environment.

Examples that closely replicate the clinical environment demonstrate that PCA was virucidal when physically engaging the SARS CoV2 virus in an aqueous medium are provided below.

Interruption of Transmission: Based upon these findings there is application for interruption of transmission in many ways. There is the application for sanitizing human skin and disinfecting personal protective equipment; e.g., face masks. Spraying the dual reagents on hard surfaces kills what is present and leave a PCA residue coating to be viricidal. The interrupts the transmission from hard surfaces to hands to the subject's face. In addition, fogging and or aerophization of trains, plane and automobiles. These methods of interruption may be used in buildings and or arenas. It may be applied to room filters.

Treatment: The present clinical significance of these observations is that PCA in fluid would retain its various crystalline shapes and therefore its anti-viral properties lend PCA to a treatment modality. This would be expected in an aerosol and body fluids. The application is available for oral, intravenous and intraperitoneal routes. It may be used in a nebulizer or ventilator.

Translation to Clinical Practice: PCA is FDA designated as safe with a Generally Recognized As Safe for food substance flavoring. PCA is safe to ingest and therefore ready for translation to clinical application. Its ready availability and low cost of goods insures a wide societal distribution.

The virus is physically disrupted when it comes in physical contact with protocatechuic acid crystals and therefore renders the virus pathologically inactivated.

PCA and related methods interrupts the transmission of the coronavirus in several ways. PCA crystals be applied topically and delivered in a liquid vehicle solution. Alcohol provides a dual effect when it is the vehicle for use as a sanitizer and or disinfectant on skin or hard surfaces. The alcohol kills what is present and after drying the residual surface PCA coating provides a continuing anti-viral function. It may be applied to hard surfaces to protect from this mode of transmission. It may be used as a coating and on application transmission is interrupted by PCA; in one embodiment it may be in a liquid vehicle, and a stabilizer.

In embodiments, the liquid vehicle comprises an alcohol and the stabilizer comprises an oil. In preferred embodiments, the oil is an essential oil. In embodiments, the compositions may comprise principally protocatechuic acid, liquid vehicle, and stabilizer as the main ingredients. In preferred embodiments, the compositions may comprise only protocatechuic acid, a liquid vehicle, and a stabilizer.

Water is the vehicle for interruption and or treatment of the mucous membranes of the nose, mouth, pharynx, respiratory tree and lungs. The compositions may be sprayed or fogged onto various products and articles of manufacture, and mammalian and human skin, to kill and protect from viruses including the Covid 19 SARS-Co-2 virus.

In preferred embodiments, the liquid vehicle includes water or a low boiling point alcohol and/or alcohol combination ranging from about 0° C. to about 100° C. The alcohol may include methanol and/or butanol, but preferably ethanol and/or propanol for human use.

Low boiling point alcohols can include alcohols such as methanol, ethanol, 1-propanol, 2-propanol, 1-butanol, 2-butanol, 2-methyl-1-propanol, 2-methyl-2-propanol, 1-pentanol, 3-methyl-1-butanol, 2,2-dimethyl-1-propanol, and cyclopentanol.

An essential oil is generally a concentrated hydrophobic liquid containing volatile (easily evaporated at normal temperatures) chemical compounds extracted from a plant. Essential oils are also known as volatile oils, ethereal oils, aetherolea, or as the oil of the plant from which they were extracted. In preferred embodiments, the essential oil may comprise orange, mint, peppermint, cedarwood, lemon, southern blue gum, evergreen, clove, and/or spearmint.

Additional possible ingredients include glycerin, propylene glycol, sodium benzoate, as well as sanitizers and disinfectants. Propylene glycol may be a vehicle for topical application and or for aerophilization. See https://ajph.aphapublications.org/doi/pdf/10.2105/AJPH.34.5.477.

One embodiment of the present disclosure provides for the spraying of protocatechuic acid (PCA) in solution on a variety of articles. Upon drying the result being a coating PCA on and or in the articles substance. The preferred embodiments are an article of manufacture including personal protective equipment (PPE). Personal protective equipment includes caps, hats, and other head coverings, gowns, masks and facemasks, gloves, shoes, and other footwear, etc. The application may be at the time of manufacture and or after-market application in the clinical setting.

The products also include hard surfaces that are frequently touched or handled by the public. This would include, as nonlimiting examples, ATM machines and credit card payment devices, gas pump handles, doors and doorknobs, tables and counters in public spaces including restaurants, etc.

In embodiments, a single spray with dual action can kill viruses including SARS-CoV-2. The first action includes an alcohol effect before evaporation. This kills the virus on contact and then dries quickly leaving a coating of PCA. The PCA coating presence on the article maintains a presence to continually kill bacteria and viruses upon subsequent contact. PCA in this application thus acts as a dual phase inhibitor.

In preferred embodiments, the virus is SARS Co 2. The alcohol will kill SARS Co 2 on contact and then the PCA coating will continue to kill and protect the surface, or article of manufacture, the subject's skin, from SARS Co 2 for a significant period of time up to at least 24 hours or more.

PCA may be used in a variety of treatments. In preferred aerosolized embodiments, the virus is SARS Co 2 is the target. An aerosolized fog with the PCA in suspension will kill SARS Co 2 on contact. Subsequently, the PCA coating will continue to kill and protect the surface, or article of manufacture, the subject, from SARS Co 2 for a significant period of time up to at least 24 hours or more.

In preferred oral ingestion embodiments the ready absorption places the PCA crystal in solution in the plasma which will kill SARS Co 2 on contact. This will last throughout the known presence of PCA in the mammalian body for several days. The PCA known metabolism is that it is subsequently found in urine and feces intact and as subsequent metabolites.

In the preferred embodiments of intraperitoneal route of application, the ready absorption places the PCA crystal in solution in the plasma which will kill SARS Co 2 on contact. This will last throughout the known presence of PCA in the mammalian body for several days. The PCA known metabolism is that it is subsequently found in urine and feces intact and as subsequent metabolites.

In the preferred embodiments of intravenous route of application, the presence places the PCA crystal in solution in the plasma which will kill SARS Co 2 on contact. This will last throughout the known presence of PCA in the mammalian body for several days. The PCA known metabolism is that it is subsequently found in urine and feces intact and as subsequent metabolites.

In preferred embodiments of a PCA coating application to room and respiratory filters and facilities, the PCA crystal in the ventilation system such that viruses are reduced or destroyed on contact.

In the preferred embodiments of the PCA coating application with a nebulizer places the PCA crystals in the subject's respiratory system such that pathologic microbes are reduced or destroyed on contact.

Also disclosed is a method of treating pathological condition caused by SARS CoV2 virus, comprising the coating of skin, oral cavity, nares, nasopharynx, and pulmonary tree.

Also disclosed is methods of treatment of the pathological condition caused by the SARS CoV2 virus comprising the intravenous and intraperitoneal route.

In embodiments, the present disclosure provides multiple routes of therapeutic delivery of PCA; e.g., coating of various products including personal protective equipment and hard surfaces. Normal size crystals (177 um) may be delivered by the oral route. Smaller sized crystals may also be used for intravenous, intraperitoneal and aerosol delivery to a patient, subject (prophylactic) or facility.

Other features and aspects will be apparent from the following detailed description, the drawings, and the claims.

DETAILED DESCRIPTION

The following detailed description is provided to assist the reader in gaining a comprehensive understanding of the methods, products, and/or systems, described herein. However, various changes, modifications, and equivalents of the methods, products, and/or systems described herein will be apparent to an ordinary skilled artisan.

Protocatechuic acid (PCA) is a phytochemical, a powerful antioxidant, which is common in nature. It is found in abundance in plants, tree leaves, and edible fruits and vegetables. PCA is naturally present in the ground, rivers, ponds, and lakes. It is manufactured by bacteria in the soil. It is present in the human diet. The metabolism in nature and the human body is known. After ingestion, injection or a topical application, the tissue and organs of residence are known. The human bowel bacteria manufacture PCA. The routes of elimination are known. There are no known human toxic effects of PCA. PCA is non-allergenic and a non-inflammatory. It is also non-mutagenic. PCA's health benefits are established in the literature and validated by supporting evidence to prior US patents. Importantly for a new therapeutic, protocatechuic acid (PCA) has been designated as Generally Recognized As Safe (GRAS) by the FDA as a flavoring substance. PCA may be biochemically manufactured and/or extracted from plants in an amorphous or crystalline state. Both states have the anti-viral properties of low pH, anti-protease, docking blocker and hormonal and cellular immunity remains inherent in the molecule.

As mentioned, protocatechuic acid (PCA) is a compound with powerful anti-inflammatory properties. One of the ways the human body responds to PCA is with a massive anti-inflammatory response. The pathological effect seen in clinical cases of SARS Co-2 has been termed a 'cytokine storm' in the lungs. PCA is a powerful anti-inflammatory by its anti-catabolic cytokine blocker properties. PCA acts as a tyrosinase inhibitor in other applications. PCA is also a protease inhibitor. PCA has anti-viral docking properties.

Protocatechuic acid (PCA) is thus a broad-spectrum antiviral destroying antibiotic when coating of cloth and/or metal surfaces. PCA has the physical properties of a crystal with sharp protrusions that may disrupt the coating of microbes in the dry state or in solution.

Protocatechuic acid (PCA) has viricidal effect on the SARS CoV2 virus as proven by the Examples provided below by a method design that replicated the clinical environment.

SARS CoV-2 virus retains its viability and pathogenesis in aqueous medium; in animals, humans and in air borne droplets. Outside of this aqueous environment SARS CoV-2 virus has an extremely limited viability. When droplets with SARS CoV-2 virus come to rest on hard surfaces, thereby subject to drying the life of the virus is just hours.

Therefore, the interruption of transmission and or treatment will be in an aqueous environment. The interruption of transmission must be designed to engage the coronavirus in such an environment; i.e. aerophilized droplets. The successful treatment will likely be likewise; within the confines of the mammalian body's nasopharynx, bronchi, lungs and vascular system.

The supporting Examples were performed in a liquid environment, replicating the clinical environment. The reagent, protocatechuic acid (PCA) was applied to an article simulating the clinical condition of spraying the article with a dual purpose. The alcohol vehicle replicated the lethal effect on contact of an existing virus on a hard surface. The residual PCA coating provided a lasting antiviral effect for subsequent viral exposure. The subsequent droplet containing virus engaged the PCA drug in an aqueous environment. There was a virucidal effect in 10 minutes of on the SARS CoV2 virus upon engaging the PCA crystal. Therefore, this Example substantiated the interruption of transmission for this drug; application to PPE, skin sanitizer, and as a disinfectant used in facility misting or fogging.

The Example design also replicated the therapeutic potential for PCA as all drug/viral engagements are in an aqueous medium. The Example design delivered the SARS CoV2 virus in the traditional droplet vehicle, hence upon contact with the PCA coated article converted the environment from dry to wet. This replicated the clinical environment of the nasopharynx, bronchi, lungs, and blood. The PCA crystals may be delivered to those anatomical locations by several known routes; oral, intravenous, and intra-peritoneal. In addition, the topical application is possible by filters in airway systems, nebulizer, or ventilators.

The translation to clinical practice is facilitated by PCA existing FDA designation as generally recognized as safe; it is edible. PCA is readily available in large quantities and the cost of goods is low.

The crystal structure of a reagent may cause physical disruption of viral coating resulting in viral death. PCA in the blood will retain its crystalline and therefore its anti-viral properties. The crystalline physical nature may be constantly changing in solution. PCA in a liquid (water and possibly alcohol or other vehicles) retains various crystalline forms of varying shapes, but with sharp edges. This crystalline anti-viral factor of PCA is present whether in a liquid vehicle or dried on a hard surface.

Mutations of a COVID-19 virus would require a generally differing therapeutic, biochemical, or chemical approach. PCA may involve physical disruption of the COVID-19 virus and low pH and so it would be expected to work against any mutations.

In embodiments, the size of PCA crystals may be approximately 177 microns. Subject to size reduction the size will differ by the method used and the source of the product. A smaller physical size is also possible. Smaller sizes may be more soluble.

In addition, PCA crystals can be subject to physical grinding or jet spraying to make into a powder. The smaller size is less than that of a human red blood cell. The rbc has a disk diameter of approximately 6.2-8.2 μm and a thickness at the thickest point of 2-2.5 μm and a minimum thickness in the center of 0.8-1 μm. This post ground size is much smaller than most human cells.

Co-crystals of PCA is another means to coat skin or hard surfaces. The solubility of PCA in water is approximately 10 mg/ml and LD50 is 800 mg/kg which makes PCA a potential co-crystal former. Seven novel cocrystals of PCA with ε-Caprolactam, Isonicotinamide, Isonicotinic acid (hydrated and anhydrate cocrystals), Theophylline, Nicotinamide and Carbamazepine are known.

One of the major proteins of COVID 19 is Mpro (main protease), also referred to as the "3C-like protease" belonging to the proteases class of hydrolytic enzymes. This enzyme plays a key role in the processing of pp1a (responsible for generating copies of viral genome) and pp1ab (responsible for generating viral genome) as involved in their proteolytic cleavage at the conserved residues among COVID 19 genome.

These can assemble to give rise to virions inside a host cell and thus, replicate to produce multiple copies. Mpro can act as potential target for structure-based drug discovery as this enzyme not only involved in autocatalytic cleavage of itself and key viral enzymes, as well as lacks any close homologues among human host. Targeting this enzyme using suitable protease small molecule inhibitor can curb virus replication and transcription which are critical steps in virus life cycle.

Molecular docking is an important tool in computer-based drug design and drug discovery which helps to predict the small ligand conformation and orientation (Docking pose) within the active sites of the target receptor protein.

Protocatechuic acid has high docking score (−9.8) and importantly protocatechuic acid derivatives show comparatively better pharmacokinetic predictions and lead likeness, along with the ease of synthesis.

PCA as one of the polyphenolic scaffolds have affinity to bind with substrate-binding pocket of COVID-19 virus Mpro, which is highly conserved among all CoV Mpros. This shows that small molecule inhibitors (PCA) targeting Mpro or in combination with other adjuvant therapies may provide an effective therapeutic regime to fight against all coronavirus associated diseases.

In embodiments, crystals of PCA can thus be placed in a liquid vehicle for delivery to a target, for example, skin or personal protective coating. Accordingly, in embodiments, the present disclosure provides coating of various products including personal protective equipment and hard surfaces. Smaller sized crystals may also be used for intravenous and aerosol delivery to a patient.

Oral and Nasal applications of PCA crystals may use water as a vehicle and, in embodiments, at a maximal concentration of about 1.24% PCA. The vehicle may be sterile water and or saline solution with a minimal amount of an essential oil or other for stability. PCA may be combined with a cellulose vehicle in nasal topical application. As mentioned, safety is inherent as PCA is FDA approved as a food flavoring additive as are the essential oils. Therefore, any entry into or beyond the oral cavity is inherently safe.

In embodiments, personal protective equipment may be coated or infused with PCA crystals. Coatings may be applied at the time of manufacture or after-market, i.e., while in use. In embodiments, an alcohol-based solution with 1 to 30% PCA may be used depending upon the intended application. The typical amount might be about 3% in a spray container, apparatus and/or mechanized delivery at manufacture of the article as with robotics and or assembly line.

In this embodiment, the alcohol vehicle causes an immediate 99% plus viral kill when wet. Upon drying, PCA crystals remain as an anti-viral coating. PCA in this form on metal and or cloth destroys SARS CoV-2 virus on contact. The anti-viral function can be based upon the PCA crystals in solution, and or dry, and cause the SARS CoV-2 virus to be dead on arrival (D.O.A.) due to subsequent contact.

In embodiments, benefits for protective masks is clear since studies have shown masks to harbor the SARS-Co-2 virus for up to 6 days. Face masks have limitations since there must be air flow for breathing. The N95 mask is promoted as the best alternative. However, those with a valve will allow particles to escape. Thereby they may protect the wearer, but if the wearer is contagious there is no protection for others. The 3M mask known as the 8511 Respirator with a Cool Flow Valve made by 3M is made for construction workers to control dust and allow for easy breathing.

The particle size of the SARS CoV-2 virus is relatively large for a virus but is less than 0.1 microns or 125 nanometers. It is noted that each particulate respirator is given a filter efficiency rating of 95, 99, or 100 when tested against particles that are the most difficult size to filter— approximately 0.3 microns in size mass median aerodynamic diameter (MMAD). NIOSH class 95 particulate respirator filters are certified to be at least 95% efficient. It is noted that 100% is not possible. Also, it is noted that the virus is 0.1 micron and the opening in this mask is 0.3 micron.

The present disclosure thus provides important additional protection for filtering. This is accomplished with a coating on the filter so that any virus passing through will be destroyed, and much more so than if no coating of PCA is present.

The disclosure further provides for spraying or wiping of surfaces including hard surfaces with PCA in an alcohol vehicle which results in immediate anti-viral removal. In addition, the anti-viral crystal coating on hard surfaces like handles, doorknobs, gas pumps will then remain and continue to kill virus for a significant period afterwards.

The supporting experimental tests described below replicate a clinical application in several ways. First, is the effectiveness of the deposit of dry crystals on hard surfaces; metal and plastic. Then the application to apply dry crystals to N95 outer mask material. Unique to the testing methods was that the virus was delivered in a liquid medium; alcohol, propylene glycol, essential oil and/or water. Therefore, the tests on virus assessed the effect of crystals of PCA in a solution to inactivate the SARS Co-2 virus in a liquid medium. This replicates the clinical transmission of the SARS Co-2 virus which is aerophilized droplets means of spreading in a liquid medium, and the virus is inactivated by the PCA crystals in solution.

As used herein, the term virucidal generally means having the capacity to or tending to destroy or inactivate viruses.

The term facility generally refers to any public facility. Businesses, hospitals, gas stations, restaurants, public rest stops, including rest rooms, etc., airports, bus stations, stadiums and public entertainment facilities, public transportation stations and vehicles, movie theaters, health care facilities, medical offices, clinics, outpatient surgery centers, and any other business or facility where the public gathers and/or transits.

The term personal protective equipment includes face coverings and masks, gowns, aprons, gloves, shoes and shoe coverings, and any other article used for personal protection particularly used to protect from the transmission of viruses and bacteria.

The term 'room' generally means an enclosed space in a building particularly public facilities and buildings, hospitals, public transportation facilities, restaurants, entertainment facility, rest stops, or any other enclosed space where the public may gather.

A stabilizer may be a chemical that is used to prevent separation or degradation. Stabilizers can include emulsifiers and surfactants, for example, for stabilization of emulsions.

As used in the specification and claims, the singular forms "a," "an," and "the" include plural referents unless the context clearly dictates otherwise. Thus, for example, reference to "a composition" includes mixtures or combinations of two or more such compositions.

Throughout the specification and claims, the word "comprise" and variations of the word, such as "comprising" and "comprises," means "including but not limited to," and is not intended to exclude, for example, other components, extracts, additives, or steps. It is also contemplated that embodiments described as "comprising" components, the invention also includes those same inventions as embodiments "consisting of" or "consisting essentially of."

Ranges can be expressed herein as "approximately" or from "about" one particular value, and/or to "about" another particular value. When such a range is expressed, another embodiment includes from the one particular value and/or to the other particular value.

A weight percent of a reagent, component, or compound unless specifically stated to the contrary, is based on the total weight of the reagent, component, composition or formulation in which the reagent, component, or compound is included, according to its usual definition.

By "reduce" or other forms of the word, such as "reducing" or "reduction," is meant decrease or lower a characteristic (e.g., inflammation, growth, or viability of viruses).

By "promote" or other forms of the word, such as "promoting," is meant to induce a particular event or characteristic, or delay the development or progression of a particular event or characteristic, or to minimize the chances that a particular event or characteristic will occur.

"Treat" or other forms of the word, such as "treating," "treatment" or treated," is used here to mean to administer a composition or to perform a method in order to induce, reduce, eliminate, and prevent a characteristic (e.g., inflammation, growth or viability of viruses). It is generally understood that treating involves providing an effective amount of the composition to the mammal or surface for treatment.

The term "vehicle" or "vehicle carrier" as used herein refers to mean the manner in which the reagents or compositions may be delivered, including as a liquid, salve, soap, foam, cream, solution, gel, spray, powder, wipes, antiviral treatments, wipes, and the like.

The term fog can generally mean a cloudlike mass or layer of minute droplets including crystals. The term fogging can mean to cover or envelop with a fog. Fogging can be accomplished with fogging or disinfecting machines well known in the art. For example, medical grade disinfecting fogging machines can preferably be used. Portable medical grade fogging machines are also preferred. Large scale industrial fogging machines can be used for large facilities like hospitals, stadiums, public entertainment facilities, etc.

A fog machine, fog generator, or smoke machine is generally a device that emits a dense vapor that appears similar to fog or smoke. An artificial fog may be used in large scale applications, and smaller, more affordable fog machines can be used for more localized applications. Fog machines typically used in a variety of industrial, training, health care, and military applications are contemplated. Typically, fog is created by vaporizing proprietary water and glycol-based or glycerin-based fluids (or through the atomization of mineral oil). This fluid (often referred to colloquially as fog juice) vaporizes or atomizes inside the fog machine. Upon exiting the fog machine and mixing with cooler outside air the vapor condenses, resulting in a thick visible fog.

Spraying is generally a fluid flying in small drops or particles for example mechanically created and blown and may be a jet of vapor or finely divided liquid and can be produced by a device (such as an atomizer or sprayer) by which the spray is created, dispersed, and/or applied.

By "additive" or "food additive" is meant to the use as a component of any food (including any substance intended to use in producing manufacturing, packing, processing, preparing, treating, packaging, transporting, or holding food).

By "antiseptic" is meant an antimicrobial reagent or composition that is applied to any surface, including skin or tissue, to effect (e.g., eliminate, inhibit, decrease or prevent) viral growth, viability, and/or survival.

By "disinfect" or other forms of the word, such as "disinfectant" or "disinfecting," is meant decrease or lower a characteristic (e.g., eliminate, reduce, inhibit, decrease, or prevent) viral growth, viability or survival at any concentration. It is generally understood that disinfect involves providing an effective amount of the composition to any surface, but particularly solid surfaces, whether smooth or porous or semi-porous, or cloth-like surfaces.

By "sanitize" or other forms of the word, such as "sanitizer" or "sanitizing," is meant decrease or lower a characteristic (e.g., eliminate, reduce, inhibit, decrease, or prevent) viral growth, viability or survival at any concentration. It is generally understood that sanitizing involves providing an effective amount of the composition to any surface. Further, it is generally understood that sanitizing solutions and sanitizing components are those solutions that may be safely used on food-processing equipment and utensils and on other food-contacting conditions.

By "sterilize" it is meant to kill on the article being sterilized. Sterilize and sterilization include cold sterilization methods.

By "isolated" or "an isolate" as it refers to either the compounds or reagents described herein means not 100% by weight but rather approximately 95% to 97% of the compound or reagent by weight.

The term "alkyl" as used herein is a branched or unbranched hydrocarbon group of 1 to 20 carbon atoms. Non limiting examples include methyl, ethyl, n-propyl, isopropyl, n-butyl, isobutyl, t-butyl, pentyl, hexyl, heptyl, octyl, nonyl, decyl, dodecyl, tetradecyl, hexadecyl, octadecyl, eicosyl, tetracosyl, and the like. Further, the alkyl group can also be substituted or unsubstituted.

The term "alkoxy" or "alkyoxy group" as used herein refers to a branched or unbranched hydrocarbon chain having from 1 to 15 carbons and linked to oxygens. Non-limiting examples include methoxy, ethoxy and the like.

The term "medicament" as used herein refers to any wound treatment, including but not limited to the group consisting of burn relief medications, anesthetic agents, wound cleansers, antiseptic agents, scar reducing agents, immunostimulating agents, antiviral agents, antikeratolytic agents, anti-inflammatory agents, antifungal agents, acne treating agents, sunscreen agents, dermatological agents, antihistamine agents, antibacterial agents, bioadhesive agents, inhibitors of prostaglandin synthesis, antioxidants, and mixtures thereof.

Unless stated to the contrary, a formula contemplates each possible isomer.

The term "nutraceutical" as used herein refers to any food stuff, including a dietary supplement or fortified food, provided for potential health and medical benefits.

The present invention also provides methods, compositions and uses for treating surfaces (solid, smooth, porous or semi-porous, or cloth-like) and liquids to reduce viral growth or to sanitize or sterilize the surface. More specifically, the methods and compositions described herein include contacting any surface with a composition comprising PCA thereby reducing or preventing viral growth on said surface, or to sanitize or sterilize the surface. The surfaces can be in the health care setting, sports setting, including stadiums, or even food preparation settings or any setting where sterile surfaces are required.

The compositions can be applied to solid surfaces such as implants, or solid surfaces like operating tables, benches, equipment, patient beds, etc. or surgical instruments to sanitize or sterilize the surface Solid surfaces such as operating tables, other equipment and other surfaces can be treated as well by spraying of the surface with compositions comprising PCA.

In addition, the compositions can be applied to smooth, porous or semi-porous, or cloth-like surfaces such as wound dressings, bedding, vascular implants, bandages, etc. The material can be treated with the PCA solution and then used immediately, or the material can be allowed to dry and then used. For example, a bandage can be treated with PCA and then allowed to dry and store (for about up to 2 years known shelf life). When needed, depending upon the nature of the wound, the bandage can either be applied directly to the wound or can be wetted with water, 70-90% isopropyl alcohol, saline or propylene glycol and/or essential oils and then applied to the wound. It is preferred to use propylene glycol and an essential oil as they enhance the absorption of PCA into the skin.

When the composition of this invention is applied to as an element of a covering or bandage, to adhere to a surface to be treated, such as a wound, the composition generally can include a concentration of the PCA of at least 1.24% and 30% by weight of the compound depending upon the chemical nature of the vehicle and the target. In certain embodiments a 25 mM concentration of PCA is applied to a bandage.

Further, the compounds of this invention will be between 20-30% by weight of the compound for one intended use and more preferably, between 1.24% and 30% by weight of the compound depending upon the chemical nature of the vehicle, the target being treated and the species of virus to be treated.

Further, the methods and compositions described herein include adding the composition comprising PCA thereof to liquid or fluid, including other sanitizing solutions and/or sanitizing components. Further still, the methods and compositions described herein include adding the composition comprising PCA to any other vehicle, including but not limited to a powder, paste, cream foam, gel, wipes, other sanitizing components and the like thereby killing, reducing or preventing viruses on said surface.

The present invention provides a composition that destroys viruses including the Covid-19 virus. The composition includes PCA. The PCA may be mixed with 70% isopropyl alcohol and or small amount of essential oil, i.e. lemon, peppermint, etc. The concentration of PCA can be anywhere from about 20% by weight PCA to 100% PCA. Preferably the concentration of PCA varies with the intended purpose from 1.24%, 20%, 30%, 20-50% or 20-40% or 20-30% by weight. When the PCA is used in a crystal form, then the crystals can be up to 100% PCA by weight. The PCA may be in the form of crystals that are embedded into a material such as a cloth or a mesh, such as titanium or stainless steel. The crystals may be applied to a surface configuration that provides for housing of the crystal on the surface. The same is for cloth material that has mesh or surface to house the physical crystals by size. They may remain in place in crystal form until activated, for example, when subject to fluid common to the mammalian body.

The amount of PCA necessary for coating metal and or cloth may be 20 to 30% PCA or 20-30 grams per 100 ml of 70% isopropyl alcohol. These compositions allow for higher concentrations, and evaporate rapidly to dry state of PCA crystals on the surface or cloth.

In another aspect of the present invention, a method of disinfecting a surface comprising contacting said surface with PCA is contemplated.

This disclosure also provides for a method comprising contacting a surface with an effective amount of the composition. By the term "effective amount" of a composition as provided herein is meant an amount of a composition sufficient to provide the desired benefit. With any prescription; onset of treatment, dose, vehicle, route, interval, frequency or duration the fundamental therapeutic action is the engagement of one or more crystals with the SARS CoV2 virus in a liquid environment; in or out of the mammalian body. As disclosed herein, the exact amount required will vary from use to use depending on a variety of processing parameters, as understood by one of ordinary skill, such as the application, type of surface, the type of virus to be treated, the surface size, the mode of delivery (e.g., aerosol, spraying or dipping), and the like. Determination of what constitutes an "effective amount" is made by routine testing with known concentrations and adjusting those concentrations as needed to obtain the desired benefit and can be determined by one of ordinary skill in the art using routine experimentation so that the PCA crystals engage the SARS CoV-2 virus.

When the antiviral composition of this invention is applied to a surface to be treated, the antiviral composition generally can include a concentration of the PCA, not including the carrier. Further, the PCA can be between 90%-97% by weight of the compound, and more preferably, between 95%-98% by weight of the compound.

When the antiviral composition or compositions of this invention are applied to a surface to be treated may be diluted for use as a sanitizer or as a preventive or prophylactically, and at greater concentrations for treatment.

In another aspect of the invention provides a method of inhibiting growth of a virus on a solid, smooth, porous or semi-porous, or cloth-like surface (such as but not limited to a cloth, wound dressing, bandage, heart or vessel grafts) by treating the surface with a composition of the present invention, preferably comprising PCA. The surface can be any solid, smooth, porous, or semi-porous, or cloth-like surface.

The present invention thus provides a composition that destroys or inhibits a virus. The composition is preferably PCA. The PCA may be mixed with 70% isopropyl alcohol. The concentration of PCA can be anywhere from about 20% PCA to 100% PCA. Preferably the concentration of PCA is about 20-50% by weight, or is about 20-40% by weight or is about 20-30% by weight or is 30% to 50% by weight. Additionally, the PCA may be in the form of crystals that are embedded into a material such as a cloth or a mesh, such as titanium or stainless steel.

The invention provides another composition comprising about 17 to 40%, or 17 to 30% or 17 to 20% by weight of PCA, isopropyl alcohol, propylene glycol and an essential oil, preferably of peppermint, or a citrus fruit (i.e. lemon, grapefruit, orange, lime, etc.). This composition is useful in the methods described in the invention, for example as a skin antiseptic as a surface disinfectant, as a spray to disinfect a surface, etc. The composition of the invention, may have at least PCA at 17+% by weight in at least 70-90% isopropyl alcohol, propylene glycol (15 mls in a 105 ml total solution) and the essential oil; i.e. peppermint or lemon etc.

The invention further provides a composition of PCA wherein the composition comprises or consists of PCA that can be applied directly or provided in various vehicles depending upon the application. A composition of 70% isopropyl alcohol, propylene glycol and essential peppermint oil may be effective in use as a skin antiseptic. Higher concentration of 10% PCA (20 grams in 90 milliliters of 70% isopropyl alcohol) may be more effective than PCA in water. The following concentration may also be effective—the composition comprising or consisting of PCA (20 grams) 70% isopropyl alcohol (85 ML), propylene glycol (15 ml) and an essential oil (5 ml).

In addition to the components and administration of said compositions disclosed above, the compositions can be in the form of an aqueous solution and also deliver PCA in suspension and or upon drying produce a residual PCA coating. The compositions disclosed herein can also be in the form of a liquid, gel, suspension, dispersion, solid, emulsion, aerosol, for example, powders, tablets, capsules, pills, liquids, suspensions, dispersions or emulsions. Also, the compositions disclosed herein can be in the form suitable for dilutions. Similarly, the compositions can be in the form of a powder, cream, paste, gel or solid that can be reconstituted.

Other components can be present in the composition, if desired. For example, the antiviral composition can also include at least one additive selected independently from a carrier, a diluent, an adjuvant, a solubilizing agent, a suspending agent, a filler, a surfactant, an antimicrobial agent, a preservative, a viscosity modifier, a thixotropy modifier, a wetting agent, an emulsifier, or any combinations thereof. For example, the disclosed antiviral composition can further comprise at least one surfactant selected from a cationic surfactant, an anionic surfactant, a non-ionic surfactant, and an amphoteric surfactant. Additionally, the disclosed antiviral and/or pharmaceutical compositions may further comprise medicament is selected from the group consisting of burn relief medications, anesthetic agents, wound cleansers, antiseptic agents, scar reducing agents, immunostimulating agents, anti-bacterial agents, biofilm destroying agents, antiviral agents, antikeratolytic agents, anti-inflammatory agents, antifungal agents, acne treating agents, sunscreen agents, dermatological agents, antihistamine agents, antibacterial agents, bioadhesive agents, inhibitors of prostaglandin synthesis, antioxidants, and mixtures thereof.

Also, the disclosed antiviral compositions can optionally include one or more additives such as carriers, adjuvants, solubilizing agents, suspending agents, diluents, surfactants, other antiviral or antimicrobial agents, preservatives, fillers, wetting agents, antifoaming agents, emulsifiers, and additives designed to affect the viscosity or ability of the composition to adhere to and/or penetrate a wound.

In one embodiment, the disclosed antiviral compositions, including the selected active components, including PCA are without causing significant undesirable biological effects or interacting in a deleterious manner with any of the other components of the composition in which it is contained.

In another embodiment, antiviral compositions of the present invention are formulated for use in liquids, solutions, gels, soaps, creams, powders, salves, and other preparations designed for topical use as antiseptic agents, sprays, foams, antibacterial treatments, wipes and the like. In another embodiment, antiseptic compositions of the present invention are formulated as a hand antiseptic, sanitizer or disinfectant.

In yet another embodiment, sanitizing compositions of the present invention are formulated for use in liquids, solutions, gels, soaps, and other preparations designed for use as sanitizing agents, liquids, including sprays, foams, gels, soaps, sanitizing treatments, and the like when used as a sanitizing solution, including but not limited to, use in food processing facilities, including food-processing equipment and utensils, and on other food-contact articles.

In yet another embodiment, sanitizing compositions of the present invention use in food processing facilities, including food-processing equipment and utensils, and on other food-contact articles are formulated to include any components generally recognized as safe for use in food processing facilities, including but not limited to, aqueous solutions containing potassium, sodium or calcium hypochlorite, a solution of hydrogen peroxide, an aqueous solution containing potassium iodide, sodium lauryl sulfate, sodium-toluenesulfonchloroamide, solutions containing dodecylbenzensulfonic acid, other acceptable detergents and the like.

In another aspect, the compositions of the present invention are used in food processing, packing, manufacturing, handling, preparing, treating, transporting, or holding as a food additive without causing undesirable effects or interacting in a deleterious manner. By way of example, protocatechuic acid can be used as an additive in meat, including the handling and processing, without causing undesirable effects or interacting in a deleterious manner with the meat.

In yet another aspect, the compositions of the present invention are used in food processing, including cold sterilization of food containers, including bottles, without causing undesirable effects or interacting in a deleterious manner.

In examples, the antiviral compositions disclosed herein can further comprise a carrier or vehicle. The term "carrier or vehicle" means a compound, composition, substance, or structure that, when in combination with a compound or composition disclosed herein, facilitates preparation, administration, delivery, effectiveness, or any other feature of the compound or composition. Examples of carriers include water, isopropyl alcohol ethanol, polyols (propyleneglycol, polyethyleneglycol, glycerol, and the like), vegetable oils, and suitable mixtures thereof. "Pharmaceutically acceptable carrier" means a compound, composition, substance, or structure that is useful in neither preparing a pharmaceutical composition which is generally safe, non-toxic, and neither biologically nor otherwise undesirable and includes that which is acceptable for veterinary as well as human pharmaceutical use.

In a further example, the antiviral compositions disclosed herein can also comprise adjuvants such as preserving, wetting, emulsifying, suspending agents, and dispensing agents.

Suitable suspending agents can include, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

The disclosed antiviral compositions can also comprise solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofur fury 1 alcohol, polyethyleneglycols and fatty acid esters of sorbitan or mixtures of these substances, and the like. The additives can be present in the disclosed compositions in any amount with the PCA.

Example 1

In one example PCA was deposited on the skin. It was staged at a higher concentration for illustrative purposes. The PCA forms a layer and protective barrier on the skin.

Example 2

In a second example, PCA crystals were applied to a metallic surface one month prior. A 2×0.5 mm bare area in the middle could not be wiped off, and the crystals were scraped off with a fingernail and some resistance. A pile up of crystals occurred on a right end of the scrape.

Example 3

In a third example a steel utensil was used in stirring a 30% concentration of PCA in ethanol. A PCA coating formed which was visible, uniform and quickly applied.

Example 4

Example 4 demonstrates the results of two independent contract laboratory studies utilizing a methodology replicating the clinical therapeutic environment whereby the PCA crystal engages the SARS CoV-2 virus in an aqueous environment. These studies demonstrate the effectiveness of Protocatechuic Acid (PCA) against SARS-CoV-2, the causative virus for COVID19.

The Test Article (TA) used for this study was Protocatechuic Acid (PCA). The TA was received as an off-white powder. The PCA solution was prepared to be 30% PCA w/v in Ethanol. The PCA was prepared in 5 g increments to pre-warmed 50-60 mL ethanol until dissolved for a total of 30 g PCA in the solution. Additional ethanol was then added volumetrically to be equivalent to 100 mL.

The Test Substrates (TS) were a Plastic-type material sourced from a clear plastic laboratory bottle (Corning 431731 Octagonal bottle, 150 mL), cloth (the top layer of a N95 mask [3M 8210]), and a Sponsor-provided wire mesh to serve as a substrate for the TA. All test substrates were cut to approximately 1"×1" in size. The test substrates were submerged into the PCA solution and dried horizontally to allow for even coating. After the substrate was thoroughly dried, the test substrate was re-submerged into the PCA solution for an additional coating.

The Test Virus used for this study was 2019 Novel Coronavirus, Isolate USA-WA1/2020 (SARS-CoV-2). The virus was stored at approximately ≤65° C. prior to use. The multiplicity of infection (MOI) was 0.01 $TCID_{50}$/cell.

The Cell Culture used for the $TCID_{50}$ test was African Green Monkey Kidney Cells (Vero E6 cells) that were maintained in Dulbecco's Minimum Essential Medium with 10% fetal calf serum (DMEM-2). All growth media contained heat-inactivated fetal calf serum and antibiotics.

The test design is shown below in Table 1. This test assesses the TA on a substrate in various conditions as shown in Table 1.

The Test Substrate was coated with PCA as described above. The test substrates was treated with PCA twice and allowed to fully dry overnight. In general, the time from the first coat to the next day's virus exposure was approximately 24 hours.

The treated Test Substrate plus TA was placed into a sterile 6 well cell culture plate and approximately 100 µL total of a ≤1×10$^6$ $TCID_{50}$/mL SARS-CoV-2 virus was such that 50 µL of virus was layered on each sides of the treated test substrates. This was the procedure used for the initial Day 1 experiment.

For the confirmatory test, in an attempt to increase the recorded titer of the controls, the treated Test Substrate plus TA was placed into a sterile 6 well cell culture plate and the same amount of virus was layered onto both sides of the test substrate. However, an addition 50 µL of DMEM was added to each side to reduce the inactivation of the virus due to desiccation. Additionally, a glass coverslip was also added to help mitigate against evaporation.

After application of the virus, the virus was contact with the Test substrates for approximately 10 minutes (Groups 1, 2, and 3, Control groups 7, 8, and 9), 60 minutes (Groups 4, 5, and 6, Control Groups 10, 11, and 12). Each substrate per time per test article was performed in duplicate.

A cell culture-only control was included to indicate that cells without any TA or virus remain healthy throughout the assay. Virus-only controls without substrate was added for each timepoint to verify that the assay was performing as expected.

After the incubation time, the treated substrate was washed with 1 mL of cell culture media (DMEM-2) for approximately 5-10 minutes within the 6 well cell culture plate and the glass cover slip removed if necessary. This was the equivalent to a 10-fold dilution. The plate was gently stirred via an orbital shaker to enhance the recovery of the virus.

For the $TCID_{50}$, the cell culture media (DMEM-2) used to wash the Test Substrate was serially diluted 10 fold and transferred into respective wells of a 96-well plate which contained a monolayer of African Green Monkey Kidney Cells (Vero E6 cells) for titration. The $TCID_{50}$ assay was performed non-GLP according to IITRI Standard Operating Procedures for the assay. The $TCID_{50}$ titers was calculated using the method of Reed-Meunch.

TABLE 1

| Study Design | | |
|---|---|---|
| Group | Test and Control Groups | PCA |
| 1 | Plastic (10 minute exposure) | 2 replicates |
| 2 | Cloth (10 minute exposure) | 2 replicates |
| 3 | Mesh (10 minute exposure) | 2 replicates |
| 4 | Plastic (60 minute exposure) | 2 replicates |
| 5 | Cloth (60 minute exposure) | 2 replicates |
| 6 | Mesh (60 minute exposure) | 2 replicates |
| 7 | Virus Control-Plastic (10 minute exposure) | 2 replicates |
| 8 | Virus Control-Cloth (10 minute exposure) | 2 replicates |
| 9 | Virus Control-Mesh (10 minute exposure) | 2 replicates |
| 10 | Virus Control-Plastic (60 minute exposure) | 2 replicates |
| 11 | Virus Control Cloth (60 minute exposure) | 2 replicates |
| 12 | Virus Control Mesh (60 minute exposure) | 2 replicates |

The Test Articles, Test Substrates and virus (SARS-CoV-2) were prepared according to protocol and each preparation was noted in the study notebook for this study.

Two experimental days were run for this study with the second day as run as a confirmatory. For Day 1, after coating the Test Substrates with PCA as described above (Groups shown in Table 1 above), a $TCID_{50}$ was performed at 10 minutes or 60 minutes after initial application of the virus. There was an observed log difference between the experimental groups (Group 1: Plastic-10 min, Group 2: Cloth-10 min, Group 3: Mesh-10 min, Group 7: Plastic-60 min, Group 8: Cloth-60 min, Group 9: Mesh-60 min) when compared to the controls (Group 4: Plastic-10 min, Group 5: Cloth-10 min, Group 6: Mesh-10 min, Group 10: Plastic-60 min, Group 11: Cloth-60 min, Group 12: Mesh-60 min)

Day 1 results observed did indicate some log reductions in infectious virus titers under the experimental conditions performed for this study when compared to controls. The results are shown below in Table 2.

TABLE 2

| | | | | Initial Experimental Run Results. | | | |
|---|---|---|---|---|---|---|---|
| Group | Test Article/ substrate | Replicate | Incubation time | $TCID_{50}$ $Log_{10}$/ mL* | Log average | St. Dev. | log difference^ |
| 1 | PCA/plastic | 1 | 10 Min | 3.75 | 3.75 | 0.00 | −0.63 |
| | PCA/plastic | 2 | 10 min | 3.75 | | | |
| 2 | PCA/Cloth | 1 | 10 min | 2.75 | 2.75 | 0.00 | −1.25 |
| | PCA/Cloth | 2 | 10 min | 2.75 | | | |
| 3 | PCA/Mesh | 1 | 10 min | 3.50 | 3.38 | 0.18 | −0.25 |
| | PCA/Mesh | 2 | 10 min | 3.25 | | | |
| 4 | Control/plastic | 1 | 10 Min | 3.75 | 4.38 | 0.88 | N/A |
| | Control/plastic | 2 | 10 min | 5.00 | | | |
| 5 | Control/Cloth | 1 | 10 min | 3.75 | 4.00 | 0.35 | N/A |
| | Control/Cloth | 2 | 10 min | 4.25 | | | |
| 6 | Control/Mesh | 1 | 10 min | 3.75 | 3.63 | 0.18 | N/A |
| | Control/Mesh | 2 | 10 min | 3.50 | | | |
| 7 | PCA/plastic | 1 | 60 Min | 3.25 | 2.88 | 0.53 | −1.13 |
| | PCA/plastic | 2 | 60 Min | 2.50 | | | |
| 8 | PCA/Cloth | 1 | 60 Min | 2.50 | 2.75 | 0.35 | −1.00 |
| | PCA/Cloth | 2 | 60 Min | 3.00 | | | |
| 9 | PCA/Mesh | 1 | 60 Min | 1.00 | 1.50 | 0.71 | −2.00 |
| | PCA/Mesh | 2 | 60 Min | 2.00 | | | |
| 10 | Control/plastic | 1 | 60 Min | 3.75 | 4.00 | 0.35 | N/A |
| | Control/plastic | 2 | 60 Min | 4.25 | | | |
| 11 | Control/Cloth | 1 | 60 Min | 4.00 | 3.75 | 0.35 | N/A |
| | Control/Cloth | 2 | 60 Min | 3.50 | | | |
| 12 | Control/Mesh | 1 | 60 Min | 3.25 | 3.50 | 0.35 | N/A |
| | Control/Mesh | 2 | 60 Min | 3.75 | | | |
| 13 | Virus control (no coupon) | N/A | 10 min | 5.75 | N/A | N/A | N/A |
| 14 | Virus control (no coupon) | N/A | 60 min | 5.75 | N/A | N/A | N/A |

*limit of detection is 1.5 $TCID_{50}$ $Log_{10}$/mL

^Log difference is defined as the averaged $TCID_{50}$ $Log_{10}$/mL from virus control on substrates - $TCID_{50}$ $Log_{10}$/mL from replicate test group. Log difference indicates amount of reduction in infectious virus when comparing the virus control on substrate to the test group.

For Day 2, after coating the Test Substrates with PCA as described above (Groups shown in Table 1 above), a $TCID_{50}$ was performed at 10 minutes or 60 minutes after initial application of the virus. There was a modification to the procedures to see if the viral titers could be increased. To mitigate against evaporation during the incubation periods, these modifications included adding an additional 50 µl of DMEM on each side of the test substrate and a glass coverslip was placed on top of the test substrate. As with the Day 1 run, there was an observed log difference between the experimental groups (Group 1: Plastic-10 min, Group 2: Cloth-10 min, Group 3: Mesh-10 min, Group 7: Plastic-60 min, Group 8: Cloth-60 min, Group 9: Mesh-60 min) when compared to the controls (Group 4: Plastic-10 min, Group 5: Cloth-10 min, Group 6: Mesh-10 min, Group 10: Plastic-60 min, Group 11: Cloth-60 min, Group 12: Mesh-60 min) as shown in Table 3, thereby confirming the results from the Day 1 run.

the experimental condition shown in the protocol after the 10 minutes and 60 minutes post-exposure incubation when compared to the virus control on substrate. From both the Day 1 and the confirmatory runs, the log reduction varied between a 0.63 to a 2.38 log reduction.

Overall, these results show that PCA when coated approximately 24 hours prior to virus exposure can reduce infectious virus performance on a substrate, however, overall effectiveness was somewhat varied between runs and test substrate. Additionally, it appears that a longer incubation time may be marginally more effective than the shorter 10 minute time. A 1 to 2 log reduction/difference corresponds to a 90 to 99% inactivation while a 3 log reduction corresponds to a 99.9% inactivation.

Example 4

The second laboratory utilized test coupons made of solid stainless steel, plastic and K95 mask were coated in 30%

TABLE 3

Confirmatory Experimental Run Results.

| Group | Test Article/ substrate | Replicate | Incubation time | $TCID_{50}$ $Log_{10}$/mL* | Log average | St. Dev. | log difference^ |
|---|---|---|---|---|---|---|---|
| 1 | PCA/plastic | 1 | 10 Min | 4.25 | 4.38 | 0.18 | −1.13 |
|   | PCA/plastic | 2 | 10 min | 4.50 |   |   |   |
| 2 | PCA/Cloth | 1 | 10 min | 4.25 | 4.25 | 0.00 | −1.13 |
|   | PCA/Cloth | 2 | 10 min | 4.25 |   |   |   |
| 3 | PCA/Mesh | 1 | 10 min | 4.75 | 4.63 | 0.18 | −1.13 |
|   | PCA/Mesh | 2 | 10 min | 4.50 |   |   |   |
| 4 | Control/plastic | 1 | 10 Min | 5.50 | 5.50 | 0.00 | N/A |
|   | Control/plastic | 2 | 10 min | 5.50 |   |   |   |
| 5 | Control/Cloth | 1 | 10 min | 5.50 | 5.38 | 0.18 | N/A |
|   | Control/Cloth | 2 | 10 min | 5.25 |   |   |   |
| 6 | Control/Mesh | 1 | 10 min | 5.75 | 5.75 | 0.00 | N/A |
|   | Control/Mesh | 2 | 10 min | 5.75 |   |   |   |
| 7 | PCA/plastic | 1 | 60 Min | 3.50 | 3.63 | 0.18 | −1.50 |
|   | PCA/plastic | 2 | 60 Min | 3.75 |   |   |   |
| 8 | PCA/Cloth | 1 | 60 Min | 2.00 | 2.75 | 1.06 | −2.38 |
|   | PCA/Cloth | 2 | 60 Min | 3.50 |   |   |   |
| 9 | PCA/Mesh | 1 | 60 Min | 4.50 | 4.38 | 0.18 | −0.88 |
|   | PCA/Mesh | 2 | 60 Min | 4.25 |   |   |   |
| 10 | Control/plastic | 1 | 60 Min | 5.00 | 5.13 | 0.18 | N/A |
|   | Control/plastic | 2 | 60 Min | 5.25 |   |   |   |
| 11 | Control/Cloth | 1 | 60 Min | 4.50 | 5.13 | 0.88 | N/A |
|   | Control/Cloth | 2 | 60 Min | 5.75 |   |   |   |
| 12 | Control/Mesh | 1 | 60 Min | 5.25 | 5.25 | 0.00 | N/A |
|   | Control/Mesh | 2 | 60 Min | 5.25 |   |   |   |
| 13 | Virus control (no coupon) | N/A | 10 min | 5.75 | N/A | N/A | N/A |
| 14 | Virus control (no coupon) | N/A | 60 min | 5.75 | N/A | N/A | N/A |

*limit of detection is 1.5 $TCID_{50}$ $Log_{10}$/mL
^Log difference is defined as the averaged $TCID_{50}$ $Log_{10}$/mL from virus control on substrates - $TCID_{50}$ $Log_{10}$/mL from replicate test group. Log difference indicates amount of reduction in infectious virus when comparing the virus control on substrate to the test group.

TABLE 4

Comparison between Initial Experimental Run to Confirmatory Run

| Test Article/ substrate | Incubation time | Day 1: Log difference | Confirmatory: Log difference |
|---|---|---|---|
| PCA/plastic | 10 Min | −0.63 | −1.13 |
| PCA/Cloth | 10 min | −1.25 | −1.13 |
| PCA/Mesh | 10 min | −0.25 | −1.13 |
| PCA/plastic | 60 Min | −1.13 | −1.50 |
| PCA/Cloth | 60 min | −1.00 | −2.38 |
| PCA/Mesh | 60 min | −2.00 | −0.88 |

A PCA coating on the three test substrates, appeared to show some effectiveness in reducing infectious virus titers in w/v PCA in 70% ethanol. Each coupon was dipped in PCA, allowed to dry, dipped again and allowed to dry with the opposite side of the coupon facing up. Once dry, 200 ul virus was added to each coupon and allowed to dry (45 minutes-1 h drying time). Virus was recovered by adding 2 ml DMEM/F12 media and washing the coupon, without scraping so as not to dislodge PCA crystals. A yellow color change in the media was observed indicating acidification of the media upon addition to the PA-coated coupon. The recovered virus was added to empty 96 well plates and diluted 1:10 down the plate. This was then added to Vero E6 cells that had grown to ~70% confluence. Cytotoxicity controls without virus and recovery controls without PCA were also done in the same manner. After addition to the cells, plates were read at day 4 for the presence of cytopathic effect (CPE) due to viral infection of cells. Note that cytotoxicity and CPE cannot be differentiated in this assay, thus any dead cells are marked as positive.

Cytotoxicity was seen up to 1:100 dilution for the K95, and 1:10 for the stainless steel and plastic coupons. Positive CPE for virus recovery controls was seen at least down to 1:10,000 dilutions for all 3 coupon materials, thus each coupon material was adequate for coupon testing. Results are shown in the table below. The SS=stainless steel, K95=K95 mask and P=plastic. +PCA means coupons coated with PCA. No PCA (e.g. SS-1) indicates virus recovery controls with no PCA coating that had virus dried and recovered.

TABLE 5

| Sample Name | Replicate # | TCID50 | TCID50/mL | Log10 TCID50 | Average TCID50 | Average Log10 TCID50 | Log Reduction to Virus Controls | Percent Log Reduction |
|---|---|---|---|---|---|---|---|---|
| SS + PCA-1 | 1 | 501.1872 | 0.01995262 | 2.70 | 298.9493 | 2.37 | 2.93 | 99.88% |
| SS + PCA-2 | 2 | 79.43282 | 0.12589254 | 1.90 | | | | |
| SS + PCA-3 | 3 | 316.2278 | 0.03162278 | 2.50 | | | | |
| SS-1 | 1 | 87992.25 | 0.00011365 | 4.94 | 226075.8 | 5.29 | | |
| SS-2 | 2 | 316227.8 | 3.1623E−05 | 5.50 | | | | |
| SS-3 | 3 | 274007.4 | 3.6495E−05 | 5.44 | | | | |
| K95 + PCA-1 | 1 | 316.2278 | 0.03162278 | 2.50 | 182.4589 | 2.10 | 2.45 | 99.65% |
| K95 + PCA-2 | 2 | 199.5262 | 0.05011872 | 2.30 | | | | |
| K95 + PCA-3 | 3 | 31.62278 | 0.31622777 | 1.50 | | | | |
| K95-1 | 1 | 58230.63 | 0.00017173 | 4.77 | 39285.11 | 4.55 | | |
| K95-2 | 2 | 19952.62 | 0.00050119 | 4.30 | | | | |
| K95-3 | 3 | 39672.07 | 0.00025207 | 4.60 | | | | |
| P + PCA-1 | 1 | 50.11872 | 0.19952623 | 1.70 | 88.00117 | 1.91 | 3.94 | 99.99% |
| P + PCA-2 | 2 | 125.8925 | 0.07943282 | 2.10 | | | | |
| P + PCA-3 | 3 | 87.99225 | 0.11364637 | 1.94 | | | | |
| P-1 | 1 | 11217075 | 8.2164E−06 | 6.09 | 971841.2 | 5.86 | | |
| P-2 | 2 | 203950 | 4.9032E−05 | 5.31 | | | | |
| P-3 | 3 | 31494498 | 6.6912E−06 | 6.17 | | | | |

While this disclosure includes specific examples, it will be apparent after an understanding of the disclosure of this application has been attained that various changes in form and details may be made in these examples without departing from the spirit and scope of the claims and their equivalents.

I claim:

1. A method of interrupting the transmission of SARS CoV2 virus comprising:
   spraying, coating, fogging, and/or infusing a subject's skin or personal protective equipment, room and/or facility, with a composition comprising protocatechuic acid, a liquid vehicle comprising an alcohol, and a stabilizer, the composition disinfecting SARS CoV2 virus on the subject's skin or personal protective equipment, room and/or facility, upon contact; and
   forming a solid coating of protocathechuic acid on the subject's skin or personal protective equipment, room and/or facility upon evaporation of the liquid vehicle, and
   disinfecting SARS CoV2 virus with the solid coating of protocatechuic acid for up to 24 hours.

2. The method of claim 1, wherein the composition is sprayed onto the mammal's skin, personal protective equipment, room, and/or facility.

3. The method of claim 1, wherein the stabilizer is an oil.

4. The method of claim 3, wherein the oil is an essential oil.

5. The method of claim 1, wherein the alcohol has a boiling point between about 50° C. and about 100° C.

6. The method of claim 5, wherein the alcohol comprises ethanol.

7. The method of claim 1, wherein an article of personal protective equipment comprises a face covering, a gown, a glove, a coat, pants, a shoe, a head covering, and/or a shirt.

8. The method of claim 1, wherein the personal protective equipment, room, and/or facility comprises a hard-outer surface and the protocatechuic acid is sprayed or coated thereon.

9. The method of claim 1, wherein the protocatechuic acid comprises protocatechuic acid crystals.

10. The method of claim 9, wherein the protocatechuic acid crystals disinfect SARS CoV2 virus in the dry state or in solution.

11. The method of claim 1, wherein the composition further comprises sodium benzoate.

12. The method of claim 1, wherein the composition further comprises glycerin.

13. The method of claim 1, wherein the composition further comprises propylene glycol.

14. The method of claim 1, wherein the composition further comprises a sanitizer and/or a disinfectant.

15. The method of claim 1, wherein the spraying, coating, fogging, and/or infusing is on human skin.

16. The method of claim 1, wherein the period of time ranges from 1 minute to 6 hours.

17. The method of claim 1, wherein the SARS-CoV-2 virus is disinfected at 99% or greater.

18. The method of claim 1, wherein the SARS-CoV-2 virus is disinfected at 99.9% or greater.

19. The method of claim 1, wherein the SARS-CoV-2 virus is disinfected at 99.99% or greater.

20. The method of claim 1, wherein the facility comprises a gas pump handle, a credit card terminal, a door, a doorknob, a table, a countertop, a handrail, and/or a button.

21. The method of claim 1, wherein the personal protective equipment is an article of clothing.

22. The method of claim 1, wherein the facility comprises a health care facility, operating table, hospital benches, hospital equipment, patient beds, and/or surgical instruments.

23. The method of claim 1, wherein the composition is a hand sanitizing composition.

24. The method of claim 1, wherein the facility comprises food handlers, food-processing equipment, food containers, bottles, and/or food utensils.

25. The method of claim 1, wherein the composition consists essentially of protocatechuic acid, a liquid vehicle comprising an alcohol, and a stabilizer.

* * * * *